United States Patent [19]

Hill

[11] 4,264,628

[45] Apr. 28, 1981

[54] PROCESS FOR THE PRODUCTION OF A YEAST AUTOLYSATE

[75] Inventor: Frank F. Hill, Dusseldorf, Fed. Rep. of Germany

[73] Assignee: Henkel Kommanditgesellschaft auf Aktien, Dusseldorf-Holthausen, Fed. Rep. of Germany

[21] Appl. No.: 64,352

[22] Filed: Aug. 7, 1979

[30] Foreign Application Priority Data

Aug. 26, 1978 [DE] Fed. Rep. of Germany ....... 2837342

[51] Int. Cl.$^3$ .............................................. A23J 1/18
[52] U.S. Cl. .......................................... 426/7; 426/60; 426/805
[58] Field of Search ..................... 426/61, 62, 60, 805, 426/807, 7, 656

[56] References Cited

U.S. PATENT DOCUMENTS

| | | | |
|---|---|---|---|
| 2,922,748 | 1/1960 | Peppler | 426/60 X |
| 2,928,740 | 3/1960 | Rosenthal et al. | 426/60 X |
| 3,809,776 | 5/1974 | Chao | 426/60 X |
| 3,934,039 | 1/1976 | Cardini et al. | 426/60 X |
| 3,961,080 | 6/1976 | Sugimoto et al. | 426/60 |
| 3,993,783 | 11/1976 | Langejan et al. | 426/60 X |
| 4,089,978 | 5/1978 | Lugay et al. | 426/60 |
| 4,118,512 | 10/1978 | Eichelburg | 426/805 X |

*Primary Examiner*—R. B. Penland
*Attorney, Agent, or Firm*—Hammond & Littell, Weissenberger and Muserlian

[57] ABSTRACT

A process for the production of a yeast autolysate consisting essentially of heating an aqueous suspension of live yeast cells to a temperature of from 20° C. to 60° C. for from 6 to 36 hours in the presence of from 0.03% to 15% by weight, based on the weight of the dry yeast mass, of a material selected from the group consisting of fatty acids having from 4 to 14 carbon atoms and their mono-, di- and tri-glyceride esters, separating the shells of the yeast cells from the liquid, evaporating said liquid and recovering a yeast autolysate.

6 Claims, No Drawings

PROCESS FOR THE PRODUCTION OF A YEAST AUTOLYSATE

BACKGROUND OF THE INVENTION

The invention relates to a process for the production of yeast autolysate, the yeast autolysates produced by the process, as well as their use in foodstuffs and feed.

Extracts from yeasts were originally used as substitutes for meat extracts for the aromatization of foods and animal feeds for pets and domesticated animals. The importance of yeast extracts as a natural aroma substance has increased in the course of the last decades. Technically extracts from yeasts can be produced in various ways. The processes differ both in their basic procedure and in the functional properties of the products obtained. The three variants for yeast extraction are plasmolysis, autolysis and hydrolysis. Production of yeast extracts by autolysis has the greatest technical importance. The production of yeast extracts by autolysis, called yeast autolysates in the following, is described in the textbook "Die Hefen" (The Yeasts), Vol. II, pp. 761–764 (published by H. Carl Nürnberg, 1962), as well as in the journal "Process Biochemistry", Vol. 1, pp. 313–317 (1966) and Vol. 5, pp. 50–52 (1970).

Suitable for the production of yeast autolysates are several genera of yeast, which are grown on different carbon sources. On an industrial scale, fast-growing yeasts of the genera Saccharomyces, Candida and Torula are cultivated on cheap carbon sources, such as molasses, malt extract, whey, sulfite liquor, ethanol and/or alkanes.

The nutrient value of living yeasts is low. Due to the separation of the yeast cell walls and due to the hydrolytic degradation of the cell content substances, the yeast autolysates have higher nutrient values and better aroma properties. The important thing in making yeast extract by means of autolysis is to start the hydrolytic degradation of the cell content substances by cell-specific enzymes without destroying the hydrolytically active enzymes by means of the necessary impulse which stimulates the living yeast to self-digestion. The hydrolytic degradation of the cell content substances can be released by destruction of the yeast cell structures by grinding or bursting. However, these processes also often release the necessary impulse to self-digestion. Suitable equipment for these process steps are known, but they require an additional high expenditure of energy. By drying the yeast before the autolysis, the cell membranes become labile and the autolysis of the resuspended yeast is supported (DOS No. 23 59 501). Most frequently, organic solvents are used for the labilization of the cell membranes and support of the autolysis ("Die Hefen", Vol II, pp. 761–764). The use of solvents such as ethanol, ethyl acetate, toluene and chlorinated hydrocarbons is preferred. In more recent processes the lysis of the yeast cells is initiated by added enzymes from various micro-organisms.

OBJECTS OF THE INVENTION

An object of the present invention is to produce a yeast autolysate while avoiding the use of expensive mechanical devices or of expensive or toxic auxiliary substances.

Another object of the present invention is the development of a process for the production of a yeast autolysate consisting essentially of heating an aqueous suspension of live yeast cells to a temperature of from 20° to 60° C. for from 6 to 36 hours in the presence of from 0.03% to 15% by weight, based on the weight of the dry yeast mass, of a material selected from the group consisting of fatty acids having from 4 to 14 carbon atoms and their mono-, di- and tri-glyceride esters, separating the yeast shells from the liquid, evaporating said liquid and recovering a yeast autolysate.

These and other objects of the invention will become more apparent as the description thereof proceeds.

DESCRIPTION OF THE INVENTION

The invention relates to a process for the production of yeast autolysate, characterized in that the autolysis of the yeast cells is carried out in aqueous suspension with addition of from 0.03% to 15% by weight, preferably from 0.1% to 6.0% by weight, based on the dry yeast substance, of fatty acids of the chain lengths $C_4$ to $C_{14}$ and/or their glycerol esters at a temperature of from 20° to 60° C. and in a time of from 6 to 36 hours, the yeast shells are separated from the liquid and the autolysate is obtained by evaporation.

More particularly, the present invention relates to a process for the production of a yeast autolysate consisting essentially of heating an aqueous suspension of live yeast cells to a temperature of from 20° to 60° C. for from 6 to 36 hours in the presence of from 0.03% to 15% by weight, based on the weight of the dry yeast mass, of a material selected from the group consisting of fatty acids having from 4 to 14 carbon atoms and their mono-, di- or tri-glyceride esters, separating the shells of the yeast cells from the liquid, evaporating said liquid and recovering a yeast autolysate.

Preferably the autolysis is carried out with addition of from 0.1% to 10% by weight, based on the dry yeast substance, of common salt to the yeast suspension. The autolysis can be accelerated or respectively the quantity of fatty acid or fatty acid glycerol ester to be used can be reduced by exposing the yeast to a thermal shock of 60° to 90° C. for 1 to 120 seconds before the autolysis. To effect this, the yeast suspension is pumped, for example, through a copper tube coil immersed in a heated water bath, the time of pumping through and the temperature of the water bath being determining for the thermal shock effect.

Application of the thermal shock process has the special advantage that thereby the required fatty acid or fatty acid glyceride quantity can be reduced to less than 0.2% by weight of the dry yeast mass. The small quantity of fatty acid then remaining in the end product does not impair the characteristic taste of the conventional yeast autolysate.

A yeast suspension containing from 10% to 20% by weight of dry yeast mass is used for the autolysis. After addition of the required quantity of fatty acid or fatty acid glyceride, the autolysis is conducted with agitation of the yeast suspension, at a temperature of 20° C. to 60° C., preferably 30° to 60° C., for 6 to 36 hours. Preferably from 0.3% to 6.0% by weight, based on the dry yeast mass, of fatty acid or fatty acid glyceride are required to obtain a good result. By application of a thermal shock the amount of fatty acid or fatty acid glyceride can be reduced to 0.03% by weight of the dry yeast mass.

The autolysate is obtained by separation of the shells of the yeast cells, e.g., by filtering or centrifuging and evaporating the aqueous solution containing the autolysate. It is advisable to rerinse the separated shells of the yeast cells several times with water or common salt solution and to combine the wash waters with the main quantity of the separated aqueous solution. The autolysate yields, as a rule, are above 30% by weight, preferably 40% to 65% by weight, based on the dry yeast mass charged.

The process is carried out with addition of fatty acids of the chain lengths $C_4$ to $C_{14}$. Preferably, saturated fatty acids are employed and more particularly caprylic and capric acids or their mixtures are used, but favorable results are obtained also with butyric acid, caproic acid, lauric acid and myristic acid. In the same manner as the free acids also their mono-, di- or tri-glycerides can be used, such as capric acid monoglyceride or caprylic acid triglyceride or, respectively, their mixtures or mixed esters. Generally the more favorable results are obtained with the free acids and with the mono- and di-glycerides.

Suitable yeast species subjected to the autolysis process are *Candida utilis, Saccharomyces cerevisiae, Saccharomyces fragilis* and *Saccharomyces carlsbergensis.*

The following examples are illustrative of the practice of the invention without being deemed limitative in any respect.

EXAMPLE 1

25 gm of a commercial pressed yeast (*Saccharomyces cerevisiae*) containing 30% dry substance were suspended in water and filled up to 50 ml in a shaking flask. 200 mg of common salt and 75 mg of the additive listed in Table 1 were added to each batch. The batches were vibrated in a water bath at 50° C. at 150 strokes per minute. After 16 hours, two samples of 5 ml were taken from each batch. Sample #1 was evaporated and dried without further treatment in an aluminum dish at 110° C. in a drying cabinet. Sample #2 was centrifuged and the sediment washed twice with 5 ml of distilled water. The combined residues after separation of the sediment were also evaporated and dried at 110° C. The dry weights shown in Table 1 show the excellent stimulating effect of capric acid or capric/caprylic acid monoglyceride on the yeast autolysis in comparison with various organic solvents.

TABLE 1

| Additive (75 mg/25 gm yeast = 0.3% by weight | Sample #1 Dry Weight Shells of Yeast Cells + Autolysate (mg) | Sample #2 Autolysate (mg) | % By Weight |
|---|---|---|---|
| — | 837.2 | 224.0 | 26.8 |
| Ethyl acetate | 867.6 | 248.3 | 28.7 |
| Toluene | 897.4 | 330.8 | 37.0 |
| Carbon tetrachloride | 856.7 | 326.6 | 38.1 |
| Trichloroethylene | 845.0 | 328.0 | 38.8 |
| Capric acid | 880.6 | 448.5 | 50.9 |
| Capric/caprylic acid - 1:1 - monoglyceride | 866.0 | 480.5 | 55.5 |

EXAMPLE 2

In a formulation carried out as in Example 1, the effect of various natural fatty acids on the yeast autolysis was tested. It is found (Table 2) that fatty acids with a number of carbon atoms from 4 to 14 are especially suitable.

TABLE 2

| Additive (75 mg/25 gm yeast = 0.3% by weight) | Sample #1 Dry Weight Shells of Yeast Cells + Autolysate (mg) | Sample #2 Autolysate (mg) | % By Weight |
|---|---|---|---|
| — | 837.2 | 224.0 | 26.8 |
| Propionic acid $C_3$ | 845.2 | 310.2 | 36.7 |
| Butyric acid $C_4$ | 844.0 | 370.5 | 43.9 |
| Valeric acid $C_5$ | 904.4 | 433.3 | 47.9 |
| Caprylic acid $C_8$ | 874.2 | 451.1 | 51.7 |
| Capric acid $C_{10}$ | 867.4 | 426.8 | 49.2 |
| Lauric acid $C_{12}$ | 843.5 | 411.5 | 48.8 |
| Myristic acid $C_{14}$ | 860.4 | 395.0 | 45.8 |
| Palmitic acid $C_{16}$ | 825.4 | 222.7 | 27.0 |

EXAMPLE 3

The amount of fatty acid required for accelerating the autolysis can clearly be reduced when the yeast cells have been subjected to a thermal shock treatment. To this end, 2.5 kg of pressed yeast (30% dry substance) were suspended in water, mixed with 100 gm of common salt, and the aqueous suspension was brought to 5.0 liters. The suspension was pumped through a coil of copper tubing which was hung in a water bath temperature-controlled at 70° C. The length of the coil and the suspension transport rate were adjusted to a 10 second residence time of the yeast suspension in the heated water bath. After passage through the metal tube, the yeast suspension was cooled in another water bath to 40° C. and then collected in a 10-liter container. The suspension was brought to a temperature of 50° C. and stirred. After about 60 minutes the batch had been pumped completely through the continuous heat shock treatment. Then the batch was mixed with 0.1% by weight of capric acid, based on the weight of the pressed yeast, and stirred for 16 hours at 50° C. The sample processing was carried out as stated in Example 1.

Additionally the taste of the end products obtained was tested. To this end, after removal of the shells of yeast cell from the autolysis batch by centrifugation, the residue was evaporated under a water jet vacuum at 60° C. (to about 70% dry substance). From the thick (viscous) autolysate a 2% solution was prepared with distilled water, which was heated to 60° C. and tasted. The two samples tasted very similar and differed only in nuances of taste. A disturbing fatty acid taste was not noticeable.

TABLE 3

| Additive 0.1% by weight referred to pressed yeast) | Sampling from Autolysis Batch After incubation time (hrs) | Sample #1 Dry Weight Shells of Yeast Cells + Autolysate (mg) | Sample #2 Autolysate (mg) | % by Weight |
|---|---|---|---|---|
| — | 1 | 952.4 | 264.2 | 27.8 |
| — | 16 | 971.2 | 455.7 | 46.9 |
| Capric acid | 2 | 944.5 | 411.3 | 43.5 |
| Capric acid | 18 | 979.0 | 606.3 | 61.9 |

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A process for the production of a yeast autolysate consisting essentially of heating an aqueous suspension of live yeast cells, said yeast selected from the group consisting of *Candida utilis, Saccharomyces cerevisiae, Saccharomyces fragilis* and *Saccharomyces carlsbergensis,* and from 0.1% to 10% by weight, based on the weight of the dry yeast mass, of common salt to a temperature of 20° to 60° C. for from 6 to 36 hours in the presence of from 0.3% to 15% by weight, based on the weight of the dry yeast mass, of a material selected from the group consisting of fatty acids having from 4 to 14 carbon atoms and their mono- and di-glyceride esters, separating ruptured shells of the yeast cells from the liquid, evaporating said liquid and recovering a yeast autolysate.

2. The process of claim 1 wherein from 0.1% to 6.0% by weight, based on the weight of the dry yeast mass, of said material is employed.

3. The process of claims 1 or 2 wherein said temperature is from 30° C. to 50° C.

4. The process of claims 1 or 2 wherein said aqueous suspension of live yeast contains from 10% to 20% by weight of dry yeast mass.

5. A process for the production of a yeast autolysate consisting essentially of subjecting to a thermal shock of 60° to 90° C. for 1 to 120 seconds an aqueous suspension of live yeast cells, said yeast cells selected from the group consisting of *Candida utilis, Saccharomyces cerevisiae, Saccharomyces fragilis* and *Saccharomyces carlsbergensis,* and from 0.1% to 10% by weight, based on the weight of the dry yeast mass of common salt, heating said aqueous suspension to a temperature of 20° to 60° C. for from 6 to 36 hours in the presence of from 0.03% to 15% by weight, based on the weight of the dry yeast mass, of a material selected from the group consisting of fatty acids having from 4 to 14 carbon atoms and their mono- and diglyceride esters, separating ruptured shells of the yeast cells from the liquid, evaporating said liquid and recovering a yeast autolysate.

6. The process of claims 1 or 5 wherein said material is selected from the group consisting of capric acid, caprylic acid, mixtures of capric acid and caprylic acids, and monoglycerides thereof.

* * * * *

UNITED STATES PATENT AND TRADEMARK OFFICE
CERTIFICATE OF CORRECTION

PATENT NO. : 4,264,628
DATED : April 28, 1981
INVENTOR(S) : FRANK F. HILL

It is certified that error appears in the above—identified patent and that said Letters Patent is hereby corrected as shown below:

Column 2, line 6 and lines 19-20: "yeast shells" should read -- shells of the yeast cells --.

Signed and Sealed this

Thirty-first Day of August 1982

[SEAL]

Attest:

GERALD J. MOSSINGHOFF

Attesting Officer        Commissioner of Patents and Trademarks